United States Patent [19]

Siskin et al.

[11] 3,948,761

[45] Apr. 6, 1976

[54] ISOMERIZATION OF ALIPHATIC HYDROCARBONS

[75] Inventors: Michael Siskin, Maplewood; Joseph J. Porcelli, Scotch Plains, both of N.J.

[73] Assignee: Exxon Research and Engineering Company, Linden, N.J.

[22] Filed: Feb. 25, 1974

[21] Appl. No.: 445,163

Related U.S. Application Data

[63] Continuation-in-part of Ser. No. 210,607, Dec. 21, 1971, abandoned.

[52] U.S. Cl. ........ 208/134; 260/666 P; 260/683.68; 260/683.7
[51] Int. Cl.² ..................... C07C 5/28; C10G 35/06
[58] Field of Search .... 208/134; 260/683.68, 683.7, 260/666 P

[56] References Cited
UNITED STATES PATENTS

| | | | |
|---|---|---|---|
| 2,410,886 | 11/1946 | Lien et al. | 260/683.68 |
| 2,433,020 | 12/1947 | Becker | 260/683.68 |
| 2,504,280 | 4/1950 | Shoemaker et al. | 260/683.68 |
| 3,201,494 | 8/1965 | Oelderik et al. | 260/683.68 |
| 3,250,819 | 5/1966 | Cabbage | 260/683.68 |

FOREIGN PATENTS OR APPLICATIONS

| | | | |
|---|---|---|---|
| 764,704 | 11/1952 | Germany | 260/683.7 |

*Primary Examiner*—Herbert Levine
*Attorney, Agent, or Firm*—Jay Simon

[57] ABSTRACT

Acyclic and alicyclic aliphatic hydrocarbons are isomerized by contacting the same with hydrogen in the presence of a difficultly reduceable metal halide in combination with at least a molar equivalent of hydrogen halide. The preferred catalyst system is tantalum pentafluoride, niobium pentafluoride or their mixtures in combination with at least a five-fold molar excess of hydrogen fluoride.

20 Claims, No Drawings

ISOMERIZATION OF ALIPHATIC HYDROCARBONS

CROSS REFERENCES TO RELATED APPLICATIONS

This application is a continuation-in-part of application, Ser. No. 210,607, filed Dec. 21, 1971 now abandoned.

BACKGROUND OF THE INVENTION

1. Field of the Invention

The present invention relates to a process for the conversion of hydrocarbon materials. More particularly, this invention relates to a catalytic process for the isomerization of saturated acyclic and alicyclic hydrocarbon materials.

2. Description of the Prior Art

Hydrocarbon conversion processes involving the use of metal halide based catalysts have been extensively described in prior art. For example, Oelderik et al, in U.S. Pat. No. 3,201,494, teach that niobium (columbium) pentafluoride or tantalum pentafluoride in combination with hydrofluoric acid can be employed for the isomerization of hexane. They also report that a catalyst based on niobium or tantalum is inferior to a hexafluoroantimonic acid catalyst. Gooswilligen et al in U.S. Pat. No. 3,617,516 also report that hexafluoroantimonic acid is an effective isomerization catalyst. Lien et al, in U.S. Pat. Nos. 2,683,763 and 2,683,764 disclose that tantalum pentafluoride or columbium pentafluoride in combination with HF can be used for the refining of hydrocarbon oils, or to promote the disproportionation of alkyl-substituted aromatic materials. The patentees also disclosed that $HF/TaF_5$ and $HF/CbF_5$ are powerful catalysts for isomerization, alkylation, cracking and other reactions. Finally, Fairbrother et al, in the Journal of the Chemical Society, pages 3051–3056 (1951) reported that the halides of niobium and tantalum, when used in combination, catalyze Friedel-Craft's type reactions.

SUMMARY OF THE INVENTION

In accordance with the present invention, it has been discovered that a catalyst combination comprising a difficultly reduceable metal halide, preferably a metal fluoride, in combination with at least a molar equivalent, preferably, a molar excess of hydrogen halide, promotes the hydroisomerization of saturated alicyclic and acyclic hydrocarbons. The catalyst system of the present invention has limited hydrocarbon solubility and is not deactivated to inactive catalyst species upon contact with hydrogen at temperatures above about 25°C. Further, the catalyst system is not inactivated when used to promote the hydroisomerization of feed stocks containing normally Friedel-Craft's catalyst poisoning amounts of unsaturated compounds, sulfur compounds and/or benzene.

The present catalyst system is effective for converting acyclic and alicyclic aliphatic hydrocarbons having at least four carbon atoms to a product enriched in an isomer thereof. Typically, acyclic hydrocarbons having at least four carbon atoms, that is, straight chain or branched chain paraffins having from about 4 to 10 carbon atoms, preferably about 4 to 8 carbon atoms, are converted to branched materials having higher octane ratings. Additionally, alicyclic hydrocarbons (naphthenes) having at least about 5 carbon atoms, typically from about 5 to 50 carbon atoms, preferably 6 to 15 carbon atoms, can be converted to isomers thereof by contacting the same with hydrogen in the presence of the catalyst system of the present invention. Mixtures of acyclic and alicyclic hydrocarbons can be used as the process feed stock. In a typical commercial operation, a paraffin stream containing mixtures of various types of open chain and closed chain paraffins is used as the process feed stock.

One of the outstanding features of the instant catalyst system is that it can be used in the presence of normally poisoning amounts of classic Friedel-Craft's catalyst poisons. For example, the process feed stock may contain amounts of unsaturated organic compounds (olefins and acetylenes), benzene, or sulfur compounds in amounts that would typically destroy the activity of classic Friedel-Craft's catalyst systems. Accordingly, the feed stock need not be purified prior to use for the removal of the above materials. By way of example, the feed stock may contain substantially any amount of benzene (or other aromatic hydrocarbons) or olefinic compounds without substantially affecting the activity of the catalyst, provided that sufficient amounts of hydrogen are present in the reaction zone to saturate that portion of the aromatics and/or olefins that would lead to catalyst deactivation. Substantially any amount of sulfur-bearing materials can also be tolerated provided that the molar ratio of sulfur compounds to metal halide does not substantially exceed about 1:1. Generally, typical Friedel-Craft's catalysts are poisoned by the presence of even relatively small amounts of unsaturated constituents, aromatics, or sulfur compounds, for example, such catalysts will be poisoned by the presence of at least 0.001 wt. % unsaturated constituents, 0.01 wt. % benzene or other aromatics, or 1 wppm sulfur compounds (wt. % based on hydrocarbon feed stock). Typical feed stocks that might be processed with the present catalyst would contain from about 0.001 to 10, more typically 0.01 to 2.0, wt. % unsaturated constituents, from 0.01 to 10, typically from 0.075 to 5.0 wt. % benzene or other aromatic materials, and from 1 to 10,000, typically from 10 to 500 wppm sulfur compounds.

Hydrogen employed in the isomerization may be derived from any suitable source. Typically, in a refinery operation, the hydrogen employed may be a crude or an impure hydrogen stream such as that obtained from a naphtha reforming operation. Again, because of the ability of the present catalyst to tolerate sulfur poisons, the hydrogen need not be purified for sulfur removal prior to use. Alternatively, hydrogen may be generated in situ by introducing hydrogen donors into the reaction zone during the course of the reaction. Examples of useful hydrogen donors include materials such as decalin, tetralin, methylcyclohexane and the like. Most preferably, elemental hydrogen is introduced into the reaction zone.

The hydroisomerization reaction may be carried out in bulk, that is, in the absence of any solvent or in the presence of a solvent or diluent material. Useful solvent or diluent compositions include fluorinated paraffins, sulfolane, sulfur dioxide, sulfurylchloride fluoride, fluorinated acids and/or acid anhydrides, HF, etc. Hydrogen fluoride is the preferred reaction diluent when the metal halide portion of the catalyst system is a metal fluoride. When hydrogen fluoride is the diluent with catalysts made up of metal chlorides or bromides, an exchange reaction results converting the metal material to the metal fluoride. When a solvent or diluent is used, sufficient amounts are employed to maintain the viscosity of the reaction mixture at a desired level. Typically, from about 0.25 to 50, preferably from about 1 to 20 volumes of solvent or diluent are used per volume of hydrocarbon feed stock.

As noted above, the instant hydroisomerization catalyst system is composed of a difficulty reduceable metal halide in combination with a hydrogen halide. Useful metal halide constituents include the fluorides, bromides and chlorides of gallium, tin, lead, vanadium, niobium, tantalum, chromium, molybdenum, tungsten and the rare earth and transuranium metals, in particular, uranium, neodymium and the chlorides and bromides of aluminum. The preferred metal halide catalyst constituents are tantalum and niobium halides, preferably tantalum pentafluoride, niobium pentafluoride and mixtures thereof.

The second component of the catalyst system is a hydrogen halide. Useful materials include hydrogen bromide, hydrogen chloride, and hydrogen fluoride. It is desirable in order to avoid exchange reactions, that the halide moiety of the hydrogen halide be one that will not cause disadvantageous exchange reactions with the metal halide constituent of the catalyst system. For example, if tantalum pentabromide is used as the metal constituent, the preferred hydrogen halide co-catalyst would be hydrogen bromide since the halogen moieties of both hydrogen chloride and hydrogen fluoride would exchange with the bromine atoms of the tantalum bromide metal constituent. Desirably, the halide moiety of the hydrogen halide and the metal halide are the same. The preferred hydrogen halide catalyst constituent is hydrogen fluoride.

Catalyst effectiveness is directed related to the molar ratio of hydrogen halide to metal halide catalyst constituent. At least an equal molar amount of hydrogen halide relative to metal halide should be present in the reaction zone. Desirably, the hydrogen halide/metal halide ratio is at least 2:1, preferably at least about 5:1. In the case of catalyst systems based on tantalum pentafluoride and niobium pentafluoride, the presence of large (5:1 to about 20:1) molar excesses of hydrogen fluoride in the reaction zone has been found to materially improve reaction rates in the presence of poisons. Depending upon the relative amounts of catalyst constituents used, the catalyst, when no support is employed, may be a homogeneous solution of hydrogen halide and metal halide or a mixture of solid and dissolved metal halide in hydrogen halide.

Except when sulfur-containing feed stocks are used, the amount of metal halide catalyst component present in the reaction zone is not critical. Typically, from about 0.001 to 10, preferably 0.01 to 5.0 weight parts of metal halide are present in the reaction zone per weight part of hydrocarbon reactant. When sulfur impurities are present in the feed stock, it is desirable, if maximum catalyst activity is desired, to have a molar excess of metal halide present in the reaction zone relative to the amount of sulfur poison present in the reaction zone at any point in time. Sulfur and sulfur compounds are believed to form complexes with the metal halide catalyst constituent. It is believed that an equilibrium is established between the amount of sulfur complex formed and the amount of sulfur in the hydrocarbon phase. Accordingly, not all of the sulfur present reacts with or complexes with the metal halide catalyst constituent. Further, the complex formation reaction appears to the reversible via an equilibrium or reaction in that the concentration of sulfur in the acid layer can be diminished when the catalyst is contacted with a sulfur-free feed stock.

As noted previously, the catalyst system of the present invention is not adversely affected by the presence of benzene or other aromatic compounds, sulfur compounds or unsaturated organic compounds. However, if maximum catalyst activity is desired, the feed stocks, diluents, and individual catalyst constituents should be purified prior to use to remove water, and/or nitrogen-containing compounds, such as amines or amonia. Nitrogen-containing compounds form stable compounds or complexes with the catalyst constituents. The The presence of small amounts of water or nitrogen-containing materials are tolerable if the corresponding catalyst loss or drop in catalyst activity is desired or can be accepted. Preferably, the water or nitrogen compound concentration within the reaction zone should not exceed about 0.01 wt. %, preferably about 1 wppm, based on total feed. Most preferably, the hydroisomerization reaction is conducted in the substantial absence of water and/or nitrogen-containing compounds.

In a typical refinery operation, the process feed stock, hydrogen and optional solvent are admixed with the catalyst in a substantially liquid phase operation. The contacting may be carried out in a plurality of serially connected mixing zones. In this type of operation, the catalyst phase and hydrocarbon phase are separated following reaction and the product recovered from unreacted feed stock utilizing conventional distillation techniques. Optionally, the metal halide, preferably metal fluoride, catalyst component may be impregnated upon an inert (to hydrogen halide) porous support material such as a fluorinated refractory oxide, fluorinated Vycor glass, graphite, polytetrafluoroethylene (Teflon) based supports as Chromosorb T and Fluoropak 80, and the feed stock and hydrogen halide co-catalyst passed over the supported metal halide in either a liquid phase, gaseous phase or mixed phase operation. Alternatively, both the hydrogen halide and metal halide catalyst materials can be impregnated upon a [HF-resistant] support material and the feed stock passed over the catalyst. In an operation wherein a support catalyst is used, the reaction liquid hourly space velocity (the liquid volume of feed per hour per volume of catalyst) would be maintained at levels of less than about 200.

Hydroisomerization reaction temperatures may vary from about 0° to 150°C.; preferably, temperatures from above about 25° – 30° to 100°C. are employed. Most preferably, the reaction is conducted at a temperature between about 30° – 60°C. In most instances, the process is conducted at a temperature varying between about 45° – 60°C. It has been discovered that isomerization reaction rates increase markedly with reaction temperature. Similarly, undesirable hydrocracking of the paraffin feed stocks also occurs at an increasing rate when elevated temperatures are used; however, this may be somewhat balanced by the use of increasing hydrogen pressures. Accordingly, the precise reaction temperature employed will entail balancing the economics for an increased reaction rate versus the debit encountered in feed stock loss to low molecular weight hydrocracked products.

The isomerization reaction is preferably conducted at a pressure sufficient to maintain the hydrocarbon feed stock and catalyst in substantially the liquid phase.

Hydrogen partial pressures in the reaction zone may vary widely and should be at least about 5 psig, preferably about 5 to 2,000 psig, more preferably 25 to 2,000, and still more preferably from about 25 to 400 psig. Typically from 0.05 to 2.5 moles, preferably from 0.05 to 1 mole, of $H_2$ per mole of hydrocarbon feed stock are present in the reaction zone. In a typical reaction system, the isomerization reaction is permitted to proceed for time periods varying from about 0.5 to 1500, preferably about 1 to 500, minutes. Of course, reaction time is interrelated with reaction temperature and hydrogen pressure and the process is conducted for a time sufficient to secure a product enriched in an isomer of at least one of the hydrocarbon components of the feed stock.

Reactions involving the use of metal fluoride/hydrogen fluoride catalyst systems can be conducted in vessels fabricated from carton steel provided that excessive temperatures are not used and provided further that the reaction system is maintained in a substantially anhydrous condition. Teflon, low carbon stainless steel (series 300) or Monel may also be used in the fabrication of reaction equipment as well as aluminum-magnesium alloys, e.g., aluminum 5052.

DESCRIPTION OF THE PREFERRED EMBODIMENTS

The following examples further illustrate the present invention. Unless otherwise specified, all percentages and parts are by weight.

EXAMPLE 1

Into a 1 liter Parr Model 4521 stirred Hastelloy C reactor, in a dry box, were placed an 80:20 molar mixture of n-hexane (209 ml., 1.60 moles) and cyclohexane (43 ml., 0.40 mole). Tantalum pentafluoride (55.2 gm., 0.2 mole) was then added to the reactor. The reactor was removed from the dry box, closed, partially evacuated by aspirator, and hydrogen fluoride (20 gm., 1 mole) was added from a lecture bottle by direct connection. The reactor was then pressurized to a hydrogen pressure of 100 psig (42 pounds of hydrogen pressure equals about 0.1 mole $H_2$) and the reaction mixture was stirred at 600 rpm for 1 hour at 50°C. A liquid sample was taken at 50°C. by connecting an evacuated 10 milliliter stainless steel cylinder to the 1 liter reactor, opening the valves connecting the two, and thereby forcing liquid through a dip stick into the smaller vessel by the difference in pressure. The sample was cooled to −70°C. and an aliquot was analyzed on an Aerograph Model 1520 Gas Chromatograph with DC 200 on Chromosorb P column (⅛ inch by 30 feet) at 90°C. The analysis showed the following distribution of products and conversion.

| Product Distribution | Area % From Gas Chromatograph Scans | Wt. % |
|---|---|---|
| ethane | 0.01 | 0.01 |
| propane | 0.11 | 0.11 |
| isobutane | 0.20 | 0.19 |
| normal-butane | 0.07 | 0.06 |
| isopentane | 0.17 | 0.16 |
| normal-pentane | 0.01 | 0.01 |
| 2,2-dimethylbutane | 28.75 | 29.24 |
| 2,3-dimethylbutane } 2-methylpentane } | 30.66 | 30.68 |
| 3-methylpentane | 10.65 | 10.69 |
| normal-hexane | 15.50 | 14.91 |
| methylcyclopentane | 2.31 | 2.32 |

-continued

| Product Distribution | Area % From Gas Chromatograph Scans | Wt. % |
|---|---|---|
| cyclohexane | 11.50 | 11.62 |
| Total | 99.16 | 100.00 |
| Conversion | Area % | Wt. % |
| i-$C_6$ | 70.06 | 70.61 |
| recovered n-$C_6$ | 15.50 | 14.91 |
| recovered methylcyclopentane + cyclohexane | 13.31 | 13.94 |
| n-$C_6$ % conversion | 80.63 | 81.36 |
| cyclohexane % conversion | 30.95 | 30.30 |

The data presented above demonstrates that at the 5:1 molar ratio, the $HF/TaF_5$ catalyst system serves to promote the substantial conversion of normal hexane to branched chain dimethylbutanes and methylpentanes. These substantial conversions were secured with only a limited amount of cracking, that is, the formation of products of lower molecular weight than normal hexane. The data also shows that the area % figures from gas chromatograph scans correspond closely to the weight % distribution of the products.

EXAMPLE 2

Employing the identical procedure used in Example 1 except that the catalyst was prepared using 26 grams of hydrogen fluoride (1.3 moles) and 25 psig of hydrogen, the following distribution of products an conversions was obtained:

| Product Distribution | Area % From Gas Chromatograph Scans |
|---|---|
| ethane | 0.02 |
| propane | 0.26 |
| isobutane | 1.21 |
| normal-butane | 0.01 |
| isopentane | 0.49 |
| normal-pentane | 0.07 |
| 2,2-dimethylbutane | 40.15 |
| 2,3-dimethylbutane } 2-methylpentane } | 30.44 |
| 3-methylpentane | 10.39 |
| normal-hexane | 6.32 |
| methylcyclopentane | 1.84 |
| cyclohexane | 8.75 |
| Total Area % | 99.95 |
| Conversion | Area % |
| i-$C_6$ | 80.98 |
| recovered n-$C_6$ | 6.32 |
| recovered methylcyclopentane + cyclohexane | 10.59 |
| n-$C_6$% conversion | 92.10 |
| cyclohexane % conversion | 47.05 |

The above data demonstrates the utility of the catalyst system of the present invention. A comparison of the results of Example 1 with the results of Example 2 illustrates that better conversions of the hexane material to dimethylbutanes is secured by increasing the $HF/TaF_5$ molar ratio. The data of both Examples 1 and 2 demonstrate that substantial quantities of the cyclohexane are hydrocracked to open chain products. Finally, the results show that the presence of relatively large quantities of cyclohexane in the reaction zone do not have an adverse affect on the catalyst system.

EXAMPLE 3

Employing the same reactor as described in Example 1, a 90:10 mixture of n-hexane (235 milliliters, 1.80 mole) and cyclohexane (21.6 milliliters, 0.20 mole) was charged. Tantalum pentafluoride (52.2 grams, 0.2 mole) was then charged to the reactor. The reactor was removed from the dry box, closed, partially evacuated by aspirator and hydrogen fluoride (21grams, 1.05 mole) was added from a lecture bottle by direct connection. The reactor was then pressurized with hydrogen to a pressure of 25 psig. The resulting mixture was heated at 122°F with stirring for three hours and a sample taken. A gas chromatograph analysis (see Example 1) indicated the following distribution of products and conversions:

| Product Distribution | Area % |
|---|---|
| ethane | 0.13 |
| propane | 0.44 |
| isobutane | 1.17 |
| normal-butane | 0.27 |
| isopentane | 0.84 |
| normal-pentane | 0.12 |
| 2,2-dimethylbutane | 42.93 |
| 2,3-dimethylbutane } 2-methylpentane | 33.10 |
| 3-methylpentane | 11.53 |
| normal-hexane | 6.82 |
| methylcyclopentane | 0.42 |
| cyclohexane | 2.23 |
| Total Area % | 100.00 |

| Conversion | Area % |
|---|---|
| i-$C_6$ | 87.56 |
| recovered n-$C_6$ | 6.82 |
| recovered methylcyclopentane + cyclohexane | 2.65 |
| n-$C_6$ % conversion | 92.42 |
| cyclohexane % conversion | 73.5 |

This experiment illustrates, when compared with the results of Example 2, the effect of decreasing the molar ratio of hydrogen fluoride to tantalum pentafluoride in the catalyst system. Specifically, a three times longer reaction period was needed to secure similar yields when reduced amounts of HF were used.

EXAMPLe 4

For purposes of comparison the following example was conducted in essentially the same manner as Example 3 except that 17 grams of hydrogen fluoride (0.9 mole) was employed and the reaction was conducted in the absence of hydrogen. The resulting distribution of products and conversions was obtained after a 1-hour reaction period summarized below.

| Product Distribution | Area % |
|---|---|
| ethane | — |
| propane | 0.22 |
| isobutane | 1.37 |
| normal-butane | 0.04 |
| isopentane | 0.68 |
| normal-pentane | 0.05 |
| 2,2-dimethylbutane | 23.25 |
| 2,3-dimethylbutane } 2-methylpentane | 22.17 |
| 3-methylpentane | 7.52 |
| normal-hexane | 38.72 |
| methylcyclopentane | 0.46 |
| cyclohexane | 5.50 |
| Total Area % | 99.98 |

| Product Distribution | Area % |
|---|---|
| Conversion | Area % |
| i-$C_6$ | 52.49 |
| recovered n-$C_6$ | 38.72 |
| recovered methylcyclopentane + cyclohexane | 5.96 |
| n-$C_6$ % conversion | 56.98 |
| cyclohexane % conversion | 40.40 |

The results of this experiment clearly demonstrate the effect of the presence of hydrogen on the efficiency of the isomerization process. A comparison of the results of this experiment with the data of Example 3 reveals that the presence of hydrogen serves to markedly increase the extent of conversion of the hexane reactant to the desirable dimethylbutane products.

EXAMPLE 5

This example illustrates the operability of the process of the present invention in the presence of typical catalyst poisons such as benzene.

To the 1 liter reactor described in Example 1 was charged n-hexane (235 milliliters, 1.80 moles), cyclohexane (21.6 milliliters, 0.20 mole) and benzene (3.55 milliliters, 0.04 mole) thereby forming a 88.24/9.80/1.96 molar mixture of reactants and catalyst poison. Tantalum pentafluoride (55.2 grams, 0.20 mole) was added to the reactor. The reactor was removed from the dry box, closed, partially evacuated by aspirator, and hydrogen fluoride (51 grams, 2.5 moles) was added. The reactor was then pressurized with hydrogen to a pressure of 75 psig and the reaction mixture was stirred at 600 rpm for 1 hour at 50°C. The resulting distribution of products and conversions secured with the process are summarized below.

| Product Distribution | Area % |
|---|---|
| ethane | 0.05 |
| propane | 0.27 |
| isobutane | 1.08 |
| normal-butane | 0.25 |
| isopentane | 0.46 |
| normal-pentane | 0.07 |
| 2,2-dimethylbutane | 43.20 |
| 2,3-dimethylbutane } 2-methylpentane | 32.27 |
| 3-methylpentane | 10.87 |
| normal-hexane | 6.82 |
| methylcyclopentane | 0.75 |
| benzene | 0.20 |
| cyclohexane | 3.78 |
| Total Area % | 100.04 |

| Conversion | Area % |
|---|---|
| i-$C_6$ | 86.31 |
| recovered n-$C_6$ | 6.82 |
| recovered methylcyclopentane + cyclohexane | 4.53 |
| n-$C_6$ % conversion | 92.27 |
| cyclohexane % conversion | 53.78 |
| benzene conversion | 89.80 |

It can be seen that hydroisomerized iso-$C_6$'s were obtained in high yield in spite of the presence of the benzene. Further, the $TaF_5$/HF catalyst served to saturated and/or hydrocrack a major portion of the benzene.

The following examples illustrate the use of mixtures of tantalum pentafluoride and niobium pentafluoride as well as niobium pentafluoride, per se, as the hydrocarbon conversion catalyst in admixture with hydrofluoric acid.

EXAMPLE 6

Employing the procedure described in Example 3, tantalum pentafluoride (27.6 grams, 0.1 mole) and niobium pentafluoride (18.8 grams, 0.1 mole) were added to the reactor. The reactor was removed from the dry box, closed, partially evacuated by aspirator and hydrogen fluoride (45 grams, 2.3 moles) was added. The reactor was then pressurized with hydrogen (0.4 gram, 0.2 mole) and the reaction mixture was stirred at 600 rpm for 2 hours at 50°C. The resulting distribution of products and conversions obtained is set forth below:

| Product Distribution | Area % |
|---|---|
| ethane | 0.04 |
| propane | 0.14 |
| isobutane | 0.25 |
| normal-butane | 0.11 |
| isopentane | 0.22 |
| normal-pentane | 0.05 |
| 2,2-dimethylbutane | 41.57 |
| 2,3-dimethylbutane 2-methylpentane | 33.65 |
| 3-methylpentane | 11.32 |
| normal-hexane | 6.42 |
| methylcyclopentane | 1.02 |
| cyclohexane | 5.22 |
| Total area % | 100.01 |

| Conversion | Area % |
|---|---|
| i-$C_6$ | 86.54 |
| recovered n-$C_6$ | 6.42 |
| recovered methylcyclopentane + cyclohexane | 6.24 |
| n-$C_6$ % conversion | 92.87 |
| cyclohexane % conversion | 37.60 |

EXAMPLE 7

Into the reactor described in Example 1 were placed a mixture of n-hexane (235 milliliters, 1.8 moles), cyclohexane (2.6 milliliters, 0.2 mole) and benzene (8.8 milliliters, 0.1 mole). Niobium pentafluoride (37.6 grams, 0.2 mole) was then added to the reactor. The reactor was removed from the dry box, closed, partially evacuated by aspirator and hydrogen fluoride (42 grams, 2.1 moles) was added. The reactor was then pressurized with hydrogen (1.2 grams, 0.7 mole) and the reaction mixture was stirred at 600 rpm for 17 hours at 50°C. The resulting distribution of products and conversions secured is set forth below:

| Product Distribution | Area % |
|---|---|
| ethane | — |
| propane | 0.11 |
| isobutane | 0.07 |
| normal-butane | 0.06 |
| isopentane normal-pentane | 0.07 |
| 2,2-dimethylbutane | 11.92 |
| 2,3-dimethylbutane 2-methylpentane | 35.75 |
| 3-methylpentane | 12.59 |
| normal-hexane | 27.87 |
| methylcyclopentane | 1.27 |
| cyclohexane | 6.82 |
| benzene | 3.45 |
| Total area % | 99.96 |

| Conversion | Area % |
|---|---|
| i-$C_6$ | 60.24 |
| recovered n-$C_6$ | 27.87 |
| recovered methylcyclopentane + cyclohexane | 8.09 |
| n-$C_6$ % conversion | 67.48 |
| cyclohexane % conversion | 15.02 |
| benzene % conversion | 27.52 |

It can be seen that high yields of isomerized and hydroisomerized products were obtained with the niobium pentafluoride/HF catalyst despite the presence of the benzene catalyst poison.

EXAMPLE 8

Example 6 was repeated using a catalyst comprising tantalum pentafluoride (5.52 grams, 0.02 mole) and niobium pentafluoride (33.52 grams, 0.18 mole). 55 grams of hydrogen fluoride (2.7 moles) was added and the reactor was pressurized with hydrogen (0.2 gram, 0.1 mole). The reaction mixture was stirred at 600 rpm for 6 hours at 50°C. The distribution of products and conversions obtained is summarized below:

| Product Distribution | Area % |
|---|---|
| ethane | — |
| propane | 0.09 |
| isobutane | 0.17 |
| normal-butane | 0.04 |
| isopentane | 0.12 |
| normal-pentane | 0.01 |
| 2,2-dimethylbutane | 38.03 |
| 2,3-dimethylbutane 2-methylpentane | 34.99 |
| 3-methylpentane | 11.96 |
| normal-hexane | 6.95 |
| methylcyclopentane | 1.34 |
| cyclohexane | 6.27 |
| Total Area % | 99.97 |

| Conversion | Area % |
|---|---|
| i-$C_6$ | 84.98 |
| recovered n-$C_6$ | 6.95 |
| recovered methylcyclopentane + cyclohexane | 7.61 |
| n-$C_6$ % conversion | 92.28 |
| cyclohexane % conversion | 23.90 |

The following examples illustrate the operability of the process of the present invention in the presence of the variety of sulfur-containing catalyst poisons.

EXAMPLE 9

Employing the procedure described in Example 3, isobutyl mercaptan (3.61 grams, 0.04 mole) amounting to about 7,000 parts per million sulfur was added to the reactor. Tantalum pentafluoride (55.2 grams, 0.20 mole) was added to the reactor. The reactor was removed from the dry box, closed, partially evacuated by aspirator and hydrogen fluoride (57 grams, 2.8 moles) was added. The reactor was pressurized with hydrogen to a pressure of about 75 psig and the reaction mixture was stirred at 600 rpm for 1 hour at 50°C. The resulting distribution of products and conversions obtained is set forth below:

| Product Distribution | Area % |
|---|---|
| ethane | 0.03 |
| propane | 0.15 |
| isobutane | 0.28 |
| normal-butane | 0.11 |

-continued

| Product Distribution | Area % |
|---|---|
| isopentane | 0.19 |
| normal-pentane | 0.02 |
| 2,2-dimethylbutane | 41.25 |
| 2,3-dimethylbutane } 2-methylpentane | 33.44 |
| 3-methylpentane | 11.33 |
| normal-hexane | 7.33 |
| methylcyclopentane | 1.16 |
| cyclohexane | 5.12 |
| Total Area % | 100.42 |

| Conversion | Area % |
|---|---|
| i-$C_6$ | 86.02 |
| recovered n-$C_6$ | 7.30 |
| recovered methylcyclo-pentane + cyclohexane | 6.28 |
| n-$C_6$ % conversion | 91.73 |
| cyclohexane % conversion | 35.92 |

It can be seen that high isomerization and hydroisomerization yields were obtained despite the presence of a sulfur bearing catalyst poison.

EXAMPLE 10

Employing the procedure described in Example 3, dimethylsulfide (2.48 grams, 0.04 mole) amounting to about 10,000 parts per million of sulfur was added to the reactor. Tantalum pentafluoride (55.2 grams, 0.20 mole) was then added to the reactor. The reactor was removed from the dry box, closed, partially evacuated by aspirator and hydrogen fluoride (48 grams, 2.4 moles) was added. The reactor was then pressurized with hydrogen to a pressure of about 50 psig and the reaction mixture stirred at 600 rpm for 1 hour at 50°C. The distribution of products and conversions obtained is set forth below:

| Product Distribution | Area % |
|---|---|
| ethane | 0.01 |
| propane | 0.16 |
| isobutane | 0.49 |
| normal-butane | 0.10 |
| isopentane | 0.26 |
| normal-pentane | 0.03 |
| 2,2-dimethylbutane | 42.52 |
| 2,3-dimethylbutane } 2-methylpentane | 32.68 |
| 3-methylpentane | 10.91 |
| normal-hexane | 6.68 |
| methylcyclopentane | 1.06 |
| cyclohexane | 5.00 |
| Total Area % | 99.98 |

| Conversion | Area % |
|---|---|
| i-$C_6$ | 86.11 |
| recovered n-$C_6$ | 6.68 |
| recovered methylcyclo-pentane + cyclohexane | 6.14 |
| n-$C_6$ % conversion | 92.43 |
| cyclohexane % conversion | 37.35 |

It can be seen that high yields of isomerized products were obtained despite the presence of large amounts of sulfur bearing catalyst poison.

EXAMPLE 11

Employing the procedure described in Example 3, thiophene (3.33 grams, 0.04 mole) amounting to about 2% by weight of the reactants was charged to the reactor. Tantalum pentafluoride (55.2 grams, 0.2 mole) was then added to the reactor. Thereafter hydrogen fluoride (52 grams, 2.6 moles) was added. The reactor was then pressurized with hydrogen to a pressure of about 75 psig and the reaction mixture was stirred at 600 rpm for 4 hours at 50°C. The distribution of products and conversions obtained is set forth below:

| Product Distribution | Area % |
|---|---|
| ethane | 0.08 |
| propane | 0.49 |
| isobutane | 1.63 |
| normal-butane | 0.24 |
| isopentane | 0.99 |
| normal-pentane | 0.16 |
| 2,2-dimethylbutane | 43.96 |
| 2,3-dimethylbutane } 2-methylpentane | 32.27 |
| 3-methylpentane | 11.21 |
| normal-hexane | 6.22 |
| methylcyclopentane | 0.43 |
| cyclohexane | 2.32 |
| Total area % | 99.57 |

| Conversion | Area % |
|---|---|
| i-$C_6$ | 87.44 |
| recovered n-$C_6$ | 6.22 |
| recovered methylcyclo-pentane + cyclohexane | 2.32 |
| n-$C_6$ % conversion | 92.95 |
| cyclohexane % conversion | 71.94 |

This example illustrates that the catalyst employed in the present invention are essentially insensitive to relatively large amounts of conventional sulfur bearing Friedel-Craft's catalyst poisons.

EXAMPLE 12

The following example illustrates that the catalyst system of the present invention can be employed in the presence of both benzene and sulfur poisons.

Employing the procedure described in Example 3, benzene (3.54 milliliters, 0.04 mole) and dimethylsulfide (0.073 milliliters, 0.001 mole) were added to the reactor. Tantalum pentafluoride (27.6 grams, 0.1 mole) and niobium pentafluoride (18.8 grams, 0.1 mole) was then added to the reactor. Thereafter, hydrogen fluoride (67 grams, 3.2 moles) was added to the reactor. The reactor was then pressurized with hydrogen (0.6 gram, 0.30 mole) and the reaction mixture was stirred at 600 rpm at 50°C. for 3 hours. The distribution of products and the conversions obtained is summarized below:

| Product Distribution | Area % |
|---|---|
| ethane | 0.06 |
| propane | 0.23 |
| isobutane | 0.49 |
| normal-butane | 0.25 |
| isopentane | 0.43 |
| normal-pentane | 0.07 |
| 2,2-dimethylbutane | 42.33 |
| 2,3-dimethylbutane } 2-methylpentane | 33.33 |
| 3-methylpentane | 11.30 |
| normal-hexane | 6.39 |
| methylcyclopentane | 0.79 |
| cyclohexane | 3.68 |
| benzene | 0.63 |
| Total area % | 99.98 |

| Conversion | Area % |
|---|---|
| i-$C_6$ | 86.96 |
| recovered n-$C_6$ | 6.39 |
| recovered methylcyclo-pentane + cyclohexane | 4.47 |
| n-$C_6$ % conversion | 92.75 |

| Product Distribution | Area % |
|---|---|
| cyclohexane % conversion | 50.85 |
| benzene % conversion | 67.86 |

It can be seen that the combined presence of these typical Friedel-Craft's catalyst poisons had essentially no effect on the ability of the catalyst system to promote a hydroisomerization reaction.

The following examples further illustrate the operability of the process of the present invention in the presence of other catalyst poisons such as olefins, phenanthrene and hexamethylbenzene.

EXAMPLE 13

Into the 1 liter reaction vessel described in Example 1 were placed n-hexane (235 milliliters, 1.80 moles) and cis-2-pentene (10.4 milliliters, 0.10 mole). Tantalum pentafluoride (55.2 grams, 0.02 mole) was then added to the reactor. The reactor was removed from the dry box, closed, partially evacuated by aspirator and hydrogen fluoride (34 grams, 1.7 moles) was added. The reactor was pressurized with hydrogen (1.0 gram, 0.5 mole) and the reaction mixture was stirred at 600 rpm for 4 hours at 50°C. The distribution of products and conversions secured after the first hour of the reaction period is set forth below:

| Product Distribution | Area % |
|---|---|
| ethane | 0.05 |
| propane | 0.59 |
| isobutane | 1.92 |
| normal-butane | 0.20 |
| isopentane | 1.77 |
| normal-pentane | 0.30 |
| 2,2-dimethylbutane | 37.81 |
| 2,3-dimethylbutane <br> 2-methylpentane | 32.21 |
| 3-methylpentane | 10.37 |
| normal-hexane | 11.04 |
| methylcyclopentane | 0.49 |
| cyclohexane | 3.46 |
| Total area % | 100.01 |

| Conversion | Area % |
|---|---|
| i-$C_6$ | 80.39 |
| recovered n-$C_6$ | 11.04 |
| recovered methylcyclopentane + cyclohexane | 3.95 |
| n-$C_6$ % conversion | 87.13 |
| cyclohexane % conversion | 58.51 |

It can be seen that the presence of the olefin poison did not adversely effect the course of the hydroisomerization reaction of the present invention.

EXAMPLE 14

Into a 1 liter reaction vessel described in Example 1, were placed n-hexane (209 milliliters, 1.60 grams), cyclohexane (43 milliliters, 0.40 mole) and phenanthrene (7.13 grams, 0.04 mole). Tantalum pentafluoride (55.2 grams, 0.2 mole) was then added to the reactor. The reactor was removed from the dry box, closed, partially evacuated by aspirator and hydrogen fluoride (55 grams, 2.8 moles) was added. The reactor was then pressurized with hydrogen (2.6 grams 1.3 moles) and the reaction mixture was stirred at 600 rpm for 4.5 hours at 50°C. The resulting distribution of products and conversons secured after the first 3 hours of the reaction period is set forth below:

| Product Distribution | Area % |
|---|---|
| ethane | 0.25 |
| propane | 0.65 |
| isobutane | 0.96 |
| normal-butane | 0.56 |
| isopentane | 1.04 |
| normal-pentane | 0.21 |
| 2,2-dimethylbutane | 40.86 |
| 2,3-dimethylbutane <br> 2-methylpentane | 33.67 |
| 3-methylpentane | 11.43 |
| normal-hexane | 6.57 |
| methylcyclopentane | 0.75 |
| cyclohexane | 3.04 |

| Conversion | Area % |
|---|---|
| i-$C_6$ | 85.96 |
| recovered n-$C_6$ | 6.57 |
| recovered methylcyclopentane + cyclohexane | 3.79 |
| n-$C_6$ % conversion | 91.62 |
| cyclohexane % conversion | 29.68 |

It can be seen that the presence of phenanthrene did not adversely affect the hydroisomerization reaction of the present invention.

EXAMPLE 15

Employing the procedure described in Example 14 but substituting hexamethylbenzene (6.5 grams, 0.04 mole) for the phenanthrene, the reactor was removed from the dry box, closed, partially evacuated by aspirator and hydrogen fluoride (44 grams, 2.2 moles) was then added to the reactor. The reactor was then pressurized with hydrogen (1.8 grams, 0.9 mole) and the reaction mixture was stirred at 600 rpm for 17 hours at 50°C. The resulting distribution of products and conversions is set forth below:

| Product Distribution | Area % |
|---|---|
| ethane | 0.26 |
| propane | 0.89 |
| isobutane | 2.26 |
| normal-butane | 0.72 |
| isopentane | 2.88 |
| normal-pentane | 0.46 |
| 2,2-dimethylbutane | 42.91 |
| 2,3-dimethylbutane <br> 2-methylpentane | 31.11 |
| 3-methylpentane | 11.00 |
| normal-hexane | 6.31 |
| methylcyclopentane | 0.09 |
| cyclohexane | 1.08 |

| Conversion | Area % |
|---|---|
| i-$C_6$ | 85.02 |
| recovered n-$C_6$ | 6.31 |
| recovered methylcyclopentane + cyclohexane | 1.17 |
| n-$C_6$ % conversion | 91.95 |
| cyclohexane % conversion | 94.03 |

It can be seen that the catalyst system of the present invention was not poisoned by the presence of hexamethylbenzene.

EXAMPLE 16

Into a 1-liter, stirred, Parr Hastelloy-C reactor was charged 250 milliliters of a light virgin naphtha feed stock boiling at atmospheric pressure between ambient temperature and 180°F., 0.20 mole (55.2 grams) of tantalum pentafluoride, 2.35 moles (47 grams) of hydrogen fluoride, and 0.2 mole (0.4 gram) of hydrogen.

The reaction mixture was stirred for 1 hour at 600 r.p.m. at a temperature of 50°C. Thereafter, a sample of the reaction mixture was taken and tested using chromatographic techniques. Specifically, a Perkin Elmer 900 gas chromatograph was employed using a 300 ft. × 0.01 inch DC 200 column. The gas chromatograph was operated at an initial column temperature of −20°C. and the column temperature was increased at a rate of 4° per minute to a final temperature of 130°C.

An analysis of the starting feedstock and product formed is set forth in the following table:

| Feed and Product Constituents | Feed, Weight % | Product, Weight % |
| --- | --- | --- |
| propane | 0.177 | 1.845 |
| isobutane | 1.895 | 5.490 |
| normal-butane | 5.117 | 5.244 |
| trans-2-butene | 0.175 | 0.179 |
| isopentane | 13.866 | 26.700 |
| normal-pentane | 17.044 | 5.466 |
| 2,2-dimethylbutane | 1.438 | 18.707 |
| cyclopentane | 1.619 | 0.949 |
| 2,3-dimethylbutane | 2.615 | 3.781 |
| 2-methylpentane | 11.353 | 9.737 |
| 3-methylpentane | 7.116 | 4.702 |
| normal-hexane | 15.435 | 2.553 |
| 2,2,3-trimethylbutane | 0.132 | — |
| methylcyclopentane | 6.408 | 1.995 |
| 2,4-dimethylpentane | 0.630 | 0.031 |
| benzene | 2.646 | 1.063 |
| cyclohexane | 4.448 | 7.922 |
| 2-methylhexane + 2,3-dimethylpentane | 2.223 | 0.146 |
| 3-methylhexane | 1.265 | 0.047 |
| trans-1,3-dimethylcyclopentane | 0.340 | 0.042 |
| cis-1,3-dimethylcyclopentane | 0.305 | — |
| trans-1,3-dimethylcyclopentane | 0.694 | 0.056 |
| normal-heptane | 1.235 | 0.023 |
| methylcyclohexane | 1.073 | 2.990 |
| $C_8$ naphthene | 0.017 | — |
| toluene | 0.374 | — |
| $C_8$ paraffin | 0.036 | — |
| 3-methylheptane | 0.036 | 0.167 |
| $C_8$ saturated | 0.029 | 0.076 |
| $C_8$ saturated | 0.013 | 0.027 |
| ethylbenzene | — | 0.059 |
|  | 99.751 | 99.997 |

As is evident from the above, the relative amounts of branched chain materials present in the product stream increased markedly over that present in the initial feed stock. For example, the concentration of isobutane, isopentane, 2,2-dimethylbutane and 2,3-dimethylbutane in the product increased relative to their concentrations in the feed, whereas, the relative concentrations of straight chain and lightly branched paraffinic materials such as normal-pentane, 2-methylpentane, 3-methylpentane, normal-hexane and normal-heptane in the product decreased relative to the amounts present in the feed. Finally, the concentration of benzene in the product stream was decreased by more than 50% relative to the amount present in the initial feed stock.

EXAMPLE 17

Utilizing the reactor of Example 16, a test was conducted to demonstrate the ability of the catalyst system of the present invention to promote the isomerization of lower molecular weight naphthenes. In the test, 250 milliliters of a typical refinery feed stock boiling between 180° and 350°F. at atmospheric pressure, 0.20 mole (55.2 grams) of tantalum pentafluoride, 1.9 moles (38 grams) of hydrogen fluoride and 0.15 mole (0.3 gram) of hydrogen were charged to the reactor. The reactor contents were heated to a temperature of 25°C. and maintained at this level for two hours. The reactor contents were agitated at a rate of 600 rpm. An analysis of the feed stock and product, as determined using a Consolidated Electrodynamics Corporation Model 2H03 C mass spectrometer, is set forth in the following table:

| Product Distribution | Feed Volume % | Product Volume % |
| --- | --- | --- |
| aromatics ($C_8 - C_{11}$) | 10.80 | 5.51 |
| naphthenes ($C_6 - C_{10}$) | 39.04 | 41.31 |
| cyclopentanes | 13.32 | 7.86 |
| cyclohexanes | 25.72 | 33.45 |
| paraffins | 45.44 | 48.82 |
| condensed naphthenes | 4.69 | 4.34 |

As is evident from the analysis, the amount of cyclopentanes present in the product stream was substantially less than the amount present in the feed. In contrast, the product stream was enriched in cyclohexanes relative to the feed stream.

EXAMPLE 18

Using the reactor of Example 16, two tests were conducted to demonstrate the ability of the catalyst system of the present invention to isomerize methylcyclopentane to cyclohexane. In each of the tests, an equal molar amount of benzene and methylcyclopentane was employed as the feed stock. In each test, the same catalyst system comprising 0.20 mole (55.2 grams) of tantalum pentafluoride and 2.6 moles (52 grams) of hydrogen fluoride was used. A hydrogen partial pressure of 50 psig was employed in both tests. The results of the tests are set forth below:

| Test | 1 | 2 |
| --- | --- | --- |
| Temperature, °C. | 25 | 50 |
| Reaction time, hours | 5 | 2 |
| Products, Volume % |  |  |
| Methylcyclopentane (MCP) | 7.92 | 11.89 |
| Cyclohexane (CyC$_6$) | 47.10 | 43.63 |
| $C_6H_6$ | 43.65 | 44.07 |
| iso-C$_6$'s | 1.34 | 0.41 |
| Total | 100.01 | 100.00 |
| % Conversion, MCP → CyC$_6$ | 85.82 | 78.72 |
| % MCP of MCP + C$_y$C$_6$ | 14.35 | 21.35 |
| % MCP at equilibrium | 9.1 | 20.0 |

As is evident from the above data, the instant catalyst system strongly promoted the conversion of methylcyclopentane to cyclohexane. The ability of the catalyst to promote this reaction is of major significance since the catalyst can be used to upgrade the feed stocks employed in hydroforming systems where it is desirable to have the maximum amount of cyclohexane present relative to methylcyclopentane. Further, it should be noted that the high conversion levels were achieved in the presence of a large molar excess of benzene (relative to catalyst). Typically, even minor quantities of benzene serves to deactivate Friedel-Craft's catalyst.

What is claimed is:
1. An isomerization process comprising:
  contacting in a reaction zone and at substantially liquid phase catalyst isomerization conditions including a temperature varying between about 0° and 150°C;
  a feed stock comprising a component selected from the group consisting of a saturated acyclic hydrocarbon having at least four carbon atoms, a saturated alicyclic hydrocarbon having at least five carbon atoms and mixtures thereof, said feed stock additionally containing a component selected from the group consisting of at least about 1 wppm, based on said feed stock, of sulfur compounds, at least about 0.001 wt. %, based on said feed stock, of an unsaturated hydrocarbon compound or mixtures thereof;

hydrogen at a partial pressure of at least about 5 psig and a catalyst system comprising a metal halide selected from the group consisting of gallium bromides and chlorides and the chlorides, bromides and fluorides of niobium, tantalum, molybdenum or tungsten in combination with at least an equal molar amount, based on the metal halide, of a hydrogen halide selected from hydrogen fluoride, hydrogen chloride, and hydrogen bromide, at least a portion of said metal halide being dissolved in said hydrogen halide.

2. The process of claim 1 wherein the molar ratio of hydrogen halide to metal halide present in said reaction zone is at least 2:1.

3. The process of claim 1 wherein said isomerization is conducted at a temperature varying from about 25° to 60°C.

4. The process of claim 1 wherein the metal halide is a metal fluoride and the hydrogen halide is hydrogen fluoride.

5. The process of claim 4 wherein the metal fluoride is tantalum pentafluoride, niobium pentafluoride or mixtures thereof.

6. The process of claim 5 wherein the molar ratio of hydrogen fluoride to metal fluoride present in the reaction zone is at least 2:1.

7. An isomerization process comprising:

contacting, in a reaction zone, and at substantially liquid phase catalyst isomerization conditions including an isomerization temperature varying between about 25°C. and 60°C.;

a feed stock comprising a component selected from the group consisting of a saturated acyclic hydrocarbon having from 4 to 10 carbon atoms, a saturated alicyclic hydrocarbon having from 5 to 15 carbon atoms or mixtures thereof, said feed stock additionally containing a component selected from the group consisting of at least about 1 wppm, based on said feed stock, of sulfur compounds, at least about 0.001 wt. %, based on said feed stock, of an unsaturated hydrocarbon feed stock, and mixtures thereof;

hydrogen at partial pressures varying from about 25 to 2,000 psig, and a catalyst system comprising tantalum pentafluoride, niobium pentafluoride or mixtures thereof in combination with hydrogen fluoride, the molar ratio of hydrogen fluoride to metal fluoride present in the reaction zone being at least 2:1, at least a portion of said metal fluoride being dissolved in said hydrogen fluoride.

8. The process of claim 7 wherein the feed stock contains from about 1 to 10,000 wppm sulfur compounds.

9. The process of claim 7 wherein the feed stock contains from about 0.001 to 10 wt. % unsaturated constituents.

10. The process of claim 9 wherein the unsaturated constituent is an aromatic present in an amount of about 0.01 to 10 wt. %.

11. The process of claim 7 wherein the molar ratio of hydrogen fluoride to metal fluoride present in the reaction zone is at least about 5:1.

12. An isomerization process comprising contacting, in a reaction zone, and at substantially liquid phase catalyst isomerization conditions including a temperature varying between about 0°C. and 150°C.:

a feed stock comprising a component selected from the group consisting of a saturated acyclic hydrocarbon having at least 4 carbon atoms, a saturated alicyclic hydrocarbon having at least 5 carbon atoms and mixtures thereof, said feed stock having not been subjected to any prior treatments for the substantial removal of olefinic compounds including benzene and said feed stock additionally containing at least about 0.001 wt. % olefinic constituents;

hydrogen at partial pressures varying from about 5 to 2,000 psig, and a catalyst system comprising a metal halide selected from the group consisting of gallium bromides and chlorides and the chlorides, bromides and fluorides of tantalum, niobium, molybdenum or tungsten in combination with at least an equal molar amount, based on metal halide, of a hydrogen halide selected from the group consisting of hydrogen fluoride, hydrogen chloride and hydrogen bromide, at least a portion of said metal halide being dissolved in said hydrogen halide.

13. The process of claim 12 wherein said isomerization is conducted at a temperature varying from about 25°C to about 60°C.

14. The process of claim 12 wherein said metal halide is a metal fluoride and said hydrogen halide is hydrogen fluoride and the molar ratio of hydrogen fluoride to metal fluoride is at least about 2:1.

15. The process of claim 12 wherein said metal halide is tantalum pentafluoride, niobium pentafluoride or mixtures thereof and said hydrogen halide is hydrogen fluoride.

16. The process of claim 12 wherein said feedstock contains from 0.01 to 10 wt. % benzene.

17. The process of claim 13 wherein said feed stock contains from 0.01 to 2 wt. % of an olefinic compound.

18. The process of claim 12 wherein said metal halide is aluminum chloride and said hydrogen halide is hydrogen chloride.

19. The process of claim 12 wherein the hydrogen pressure varies from about 25 to 400 psig.

20. The process of claim 10 wherein the aromatic is benzene.

* * * * *